(12) United States Patent
Haar et al.

(10) Patent No.: US 7,731,900 B2
(45) Date of Patent: Jun. 8, 2010

(54) BODY FLUID TESTING DEVICE

(75) Inventors: Hans-Peter Haar, Wiesloch (DE); Joachim Hoenes, Zwingenberg (DE); Hans List, Hesseneck-Kailbach (DE); Maria Manser, Schwetzingen (DE); Karl Miltner, Frankenthal (DE); Rudolf Pachl, Ellerstadt (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1033 days.

(21) Appl. No.: 11/124,591

(22) Filed: May 6, 2005

(65) Prior Publication Data

US 2005/0201897 A1 Sep. 15, 2005

Related U.S. Application Data

(63) Continuation of application No. PCT/EP03/13298, filed on Nov. 26, 2003.

(30) Foreign Application Priority Data

Nov. 26, 2002 (EP) .................................. 02026242

(51) Int. Cl.
*G01N 21/00* (2006.01)
(52) U.S. Cl. ........................ 422/66; 422/55; 422/56; 422/57; 422/63; 422/64; 422/65; 422/67; 422/99; 422/100; 600/583; 600/584; 436/92; 436/110; 436/901
(58) Field of Classification Search ......... 600/583–584; 422/55–57, 63–68, 99–100; 436/92, 110, 436/901
See application file for complete search history.

(56) References Cited

U.S. PATENT DOCUMENTS

| 2,714,890 A | 8/1955 | Vang |
| 3,086,288 A | 4/1963 | Balamuth et al. |
| 3,208,452 A | 9/1965 | Stern |
| 3,298,789 A | 1/1967 | Mast |
| 3,673,475 A | 6/1972 | Britton, Jr. |
| 3,802,842 A | 4/1974 | Lange et al. |
| 3,832,776 A | 9/1974 | Sawyer |
| 4,061,468 A | 12/1977 | Lange et al. |
| 4,077,406 A | 3/1978 | Sandhage et al. |

(Continued)

FOREIGN PATENT DOCUMENTS

DE 42 34 553 A1 4/1993

(Continued)

*Primary Examiner*—Jyoti Nagpaul
(74) *Attorney, Agent, or Firm*—Woodard, Emhart, Moriarty, McNett & Henry LLP

(57) ABSTRACT

The present invention concerns a body fluid testing device (10) for analyzing a body fluids, comprising a test media tape (30) adapted to collect the body fluid, a supply portion (100) storing an uncontaminated section of the test media tape, a storage portion (110) for storing a contaminated section of the test media tape, an exposure portion positioned between the supply portion and the storage portion, the exposure portion being adapted to expose a section of the test media tape to the body fluid. An important aspect is a tip portion (20) for exposing a test medium to body fluid application. The application further concerns a test media cassette for housing test media. Another aspect is a testing device and method that employs illumination of a test medium at the site for body fluid application.

31 Claims, 7 Drawing Sheets

U.S. PATENT DOCUMENTS

| | | |
|---|---|---|
| 4,154,228 A | 5/1979 | Feldstein et al. |
| 4,203,446 A | 5/1980 | Hofert et al. |
| 4,218,421 A | 8/1980 | Mack, Jr. et al. |
| 4,223,674 A | 9/1980 | Fluent et al. |
| 4,230,118 A | 10/1980 | Holman et al. |
| 4,356,826 A | 11/1982 | Kubota |
| 4,449,529 A | 5/1984 | Burns et al. |
| 4,462,405 A | 7/1984 | Ehrlich |
| 4,490,465 A | 12/1984 | Limbach et al. |
| 4,518,384 A | 5/1985 | Tarello et al. |
| 4,535,773 A | 8/1985 | Yoon |
| 4,553,541 A | 11/1985 | Burns |
| 4,627,445 A | 12/1986 | Garcia et al. |
| 4,637,403 A | 1/1987 | Garcia et al. |
| 4,653,513 A | 3/1987 | Dombrowski |
| 4,750,489 A | 6/1988 | Berkman et al. |
| 4,787,398 A | 11/1988 | Garcia et al. |
| 4,794,926 A | 1/1989 | Munsch et al. |
| 4,823,806 A | 4/1989 | Bajada |
| 4,924,879 A | 5/1990 | O'Brien |
| 4,994,068 A | 2/1991 | Hufnagle |
| 4,995,402 A | 2/1991 | Smith et al. |
| 5,029,583 A | 7/1991 | Meserol et al. |
| 5,035,704 A | 7/1991 | Lambert et al. |
| 5,047,044 A | 9/1991 | Smith et al. |
| 5,053,199 A | 10/1991 | Keiser et al. |
| 5,077,010 A | 12/1991 | Ishizaka et al. |
| 5,097,810 A | 3/1992 | Fishman et al. |
| 5,145,565 A | 9/1992 | Kater et al. |
| 5,152,775 A | 10/1992 | Ruppert |
| 5,188,118 A | 2/1993 | Terwilliger |
| 5,189,751 A | 3/1993 | Giuliani et al. |
| 5,222,504 A | 6/1993 | Solomon |
| 5,228,972 A | 7/1993 | Osaka et al. |
| 5,279,294 A | 1/1994 | Anderson et al. |
| 5,304,468 A | 4/1994 | Phillips et al. |
| 5,307,263 A | 4/1994 | Brown |
| 5,320,808 A | 6/1994 | Holen et al. |
| 5,366,470 A | 11/1994 | Ramel |
| 5,368,047 A | 11/1994 | Suzuki et al. |
| 5,415,169 A | 5/1995 | Siczek et al. |
| 5,418,142 A | 5/1995 | Kiser et al. |
| 5,451,350 A | 9/1995 | Macho et al. |
| 5,472,427 A | 12/1995 | Rammler |
| 5,474,084 A | 12/1995 | Cunniff |
| 5,514,152 A | 5/1996 | Smith |
| 5,515,170 A | 5/1996 | Matzinger et al. |
| 5,522,255 A | 6/1996 | Neel et al. |
| 5,529,074 A | 6/1996 | Greenfield |
| 5,575,403 A | 11/1996 | Charlton et al. |
| 5,580,794 A | 12/1996 | Allen |
| 5,630,986 A | 5/1997 | Charlton et al. |
| 5,632,410 A | 5/1997 | Moulton et al. |
| 5,648,047 A * | 7/1997 | Kardish et al. ............ 422/56 |
| 5,686,829 A | 11/1997 | Girault |
| 5,700,695 A | 12/1997 | Yassinzadeh et al. |
| 5,714,390 A | 2/1998 | Hallowitz et al. |
| 5,720,924 A | 2/1998 | Eikmeier et al. |
| 5,738,244 A | 4/1998 | Charlton et al. |
| RE35,803 E | 5/1998 | Lange et al. |
| 5,758,643 A | 6/1998 | Wong et al. |
| 5,776,157 A | 7/1998 | Thorne et al. |
| 5,776,719 A | 7/1998 | Douglas et al. |
| 5,788,651 A | 8/1998 | Weilandt |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,824,491 A | 10/1998 | Priest et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,857,983 A | 1/1999 | Douglas et al. |
| 5,863,800 A | 1/1999 | Eikmeier et al. |
| 5,871,494 A | 2/1999 | Simons et al. |
| 5,872,713 A * | 2/1999 | Douglas et al. ............ 702/85 |
| 5,879,311 A | 3/1999 | Duchon et al. |
| 5,880,829 A | 3/1999 | Kauhaniemi et al. |
| 5,885,211 A | 3/1999 | Eppstein et al. |
| 5,891,053 A | 4/1999 | Sesekura |
| 5,916,229 A | 6/1999 | Evans |
| 5,935,075 A | 8/1999 | Casscells et al. |
| 5,938,679 A | 8/1999 | Freeman et al. |
| 5,951,492 A | 9/1999 | Douglas et al. |
| 5,951,493 A | 9/1999 | Douglas et al. |
| 5,951,582 A | 9/1999 | Thorne et al. |
| 5,962,215 A | 10/1999 | Douglas et al. |
| 5,964,718 A | 10/1999 | Duchon et al. |
| 5,968,063 A | 10/1999 | Chu et al. |
| 5,971,941 A | 10/1999 | Simons et al. |
| 5,997,561 A | 12/1999 | Bocker et al. |
| 6,027,459 A | 2/2000 | Shain et al. |
| 6,036,924 A | 3/2000 | Simons et al. |
| 6,048,352 A | 4/2000 | Douglas et al. |
| 6,071,294 A | 6/2000 | Simons et al. |
| 6,086,545 A | 7/2000 | Roe et al. |
| 6,093,156 A | 7/2000 | Cunningham et al. |
| 6,099,484 A | 8/2000 | Douglas et al. |
| 6,117,630 A | 9/2000 | Reber et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,193,673 B1 | 2/2001 | Viola et al. |
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,245 B1 | 7/2001 | Kawai et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |

| | | | | | | |
|---|---|---|---|---|---|---|
| 6,503,210 | B1 | 1/2003 | Hirao et al. | EP | 0 351 891 B1 | 1/1990 |
| 6,506,575 | B1 | 1/2003 | Knappe et al. | EP | 0 608 820 A1 | 8/1994 |
| 6,530,892 | B1 | 3/2003 | Kelly | EP | 0 823 636 A2 | 2/1998 |
| 6,988,996 | B2 * | 1/2006 | Roe et al. .................. 600/584 | JP | H06-033413 Y | 8/1989 |
| 2001/0031931 | A1 | 10/2001 | Cunningham et al. | JP | 04194660 A1 | 7/1992 |
| 2002/0002344 | A1 | 1/2002 | Douglas et al. | JP | H06-222057 A | 8/1994 |
| 2002/0004196 | A1 | 1/2002 | Whitson | JP | 9-276235 | 10/1997 |
| 2002/0052618 | A1 | 5/2002 | Haar et al. | JP | H10-148635 A | 6/1998 |
| 2002/0082543 | A1 | 6/2002 | Park et al. | JP | 2000116768 A2 | 4/2000 |
| 2002/0103499 | A1 | 8/2002 | Perez et al. | WO | WO 93/02720 A1 | 2/1993 |
| 2003/0088191 | A1 | 5/2003 | Freeman et al. | WO | WO 93/12726 | 7/1993 |
| 2003/0233112 | A1 | 12/2003 | Alden et al. | WO | WO 97/42888 | 11/1997 |
| 2003/0233113 | A1 | 12/2003 | Alden et al. | WO | WO 01/00090 A1 | 1/2001 |
| | | | | WO | WO 01/08551 A1 | 2/2001 |
| | | FOREIGN PATENT DOCUMENTS | | WO | WO 01/34029 A1 | 5/2001 |
| | | | | WO | WO 01/66010 | 9/2001 |
| DE | 198 19 407 A1 | 11/1999 | | WO | WO 02/056769 A1 | 7/2002 |
| DE | 198 49 539 A1 | 5/2000 | | WO | WO 2004/047642 A1 | 6/2004 |
| DE | 198 57 426 A1 | 6/2000 | | | | |
| DE | 101 05 549 A1 | 8/2002 | | * cited by examiner | | |

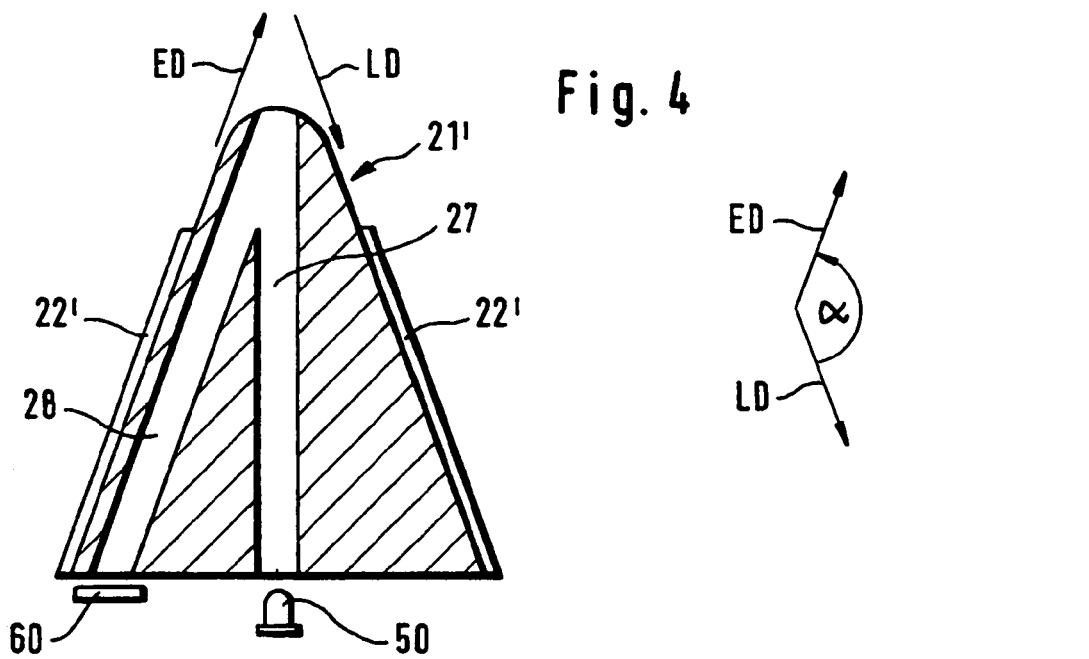
Fig. 4
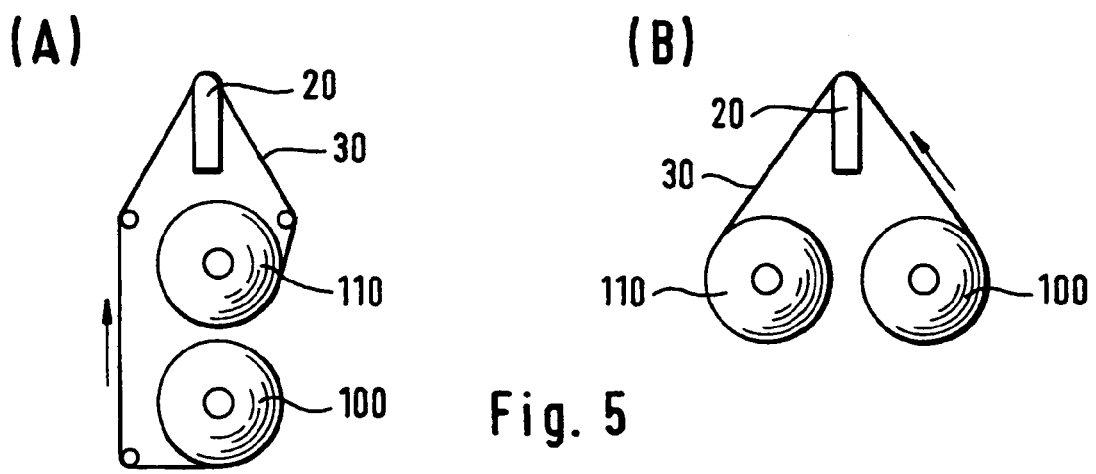
Fig. 5
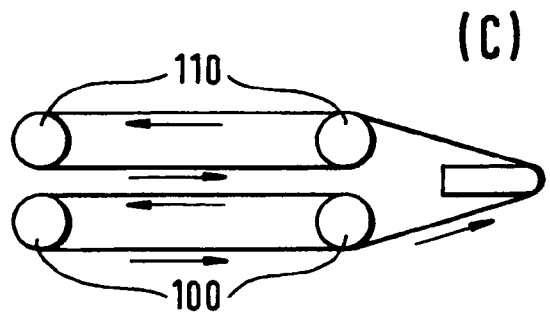

BODY FLUID TESTING DEVICE

REFERENCE TO RELATED APPLICATIONS

The present application is a continuation of International Patent Application No. PCT/EP2003/013298, filed Nov. 26, 2003, which claims foreign priority to European Patent Application No. 02 026 242.4, filed Nov. 26, 2002, which are hereby incorporated by reference in their entirety.

BACKGROUND OF THE INVENTION

The present invention relates to body fluid testing devices and more specifically, but not exclusively, concerns a body fluid testing device that incorporates a test media cassette which contains test media used to test body fluid.

General Fluid Testing

The acquisition and testing of body fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various body fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of body fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a body fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the body fluid from the incision site.

Various methods and systems for incising the skin are known in the art. Exemplary lancing devices are shown, for example, in U.S. Pat. No. Re 35,803, issued to Lange, et al. on May 19, 1998; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of body fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of body fluid from an incision is the Amira AtLast blood glucose system.

Sampling

The acquisition of the produced body fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The body fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the body fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a body fluid, test systems are commonly used which take advantage of an oxidation/reduction reaction which occurs using an oxidase/peroxidase detection chemistry. The test reagent is exposed to a sample of the body fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing body fluids for properties on constituents.

Testing Media

As mentioned above, diabetics typically have to monitor their blood glucose levels throughout the day so as to ensure that their blood glucose remains within an acceptable range. Some types sampling devices require the use of testing strips that contain media for absorbing and/or testing the body fluid, such as blood. After testing, the testing media contaminated with blood can be considered a biohazard and needs to be readily disposed in order to avoid other individuals from being exposed to the contaminated test strip. This can be especially inconvenient when the person is away from home, such as at restaurant. Moreover, individual test elements can become easily mixed with other test strips having different expiration dates. The use of expired test elements may create false readings, which can result in improper treatment of the patient, such as improper insulin dosages for diabetics.

Test Media Cassettes

Analytical systems with test media cassettes which allow multiple testing have been previously described (see e.g. U.S. Pat. No. 4,218,421 and U.S. Pat. No. 5,077,010) for the environment of automated laboratory systems which use pipettes to apply sample fluid to the test media. These systems are therefore not suited to be used by lay people as e.g. diabetics for self testing. DE 198 19 407 describes a test element cassette for use in the home environment. FIG. 1 describes a tape of electrochemical test elements having punched out regions that are presented for blood application when a test element of the tape is moved over a bended surface. FIG. 2 of DE 198 19 407 shows a test cassette with a tape of test media for reflectometric analysis. Application of sample fluid, especially body fluid which is located at a body portion is cumbersome with the shown apparatus.

It was an aim of the present invention to facilitate user handling for body fluid testing.

SUMMARY OF THE INVENTION

The present invention provides various devices and methods for testing body fluid. The present invention encompasses a body fluid testing device that contains a plurality of test media.

In accordance with one aspect of the present invention, there is provided a body fluid testing device for analyzing a body fluid. The testing device includes a test media cassette that includes a test media tape adapted to collect the body fluid. The cassette includes a supply portion that stores an uncontaminated section of the test media tape. A storage portion for storing a contaminated section of the test media tape is further employed.

The testing device is a handheld device that can be conveniently handled by an user. The test media tape may be a part of the testing device so that the whole device is discarded when the test media tape is used up or the test media tape may be arranged in a disposable cassette which is received in the testing device. An important aspect of a first embodiment of the present invention is that a portion of the test media tape onto which body fluid will be applied is exposed in a tip like shape. For this purpose the test media tape is guided over a convex tip portion which may belong to the testing device or to the test media cassette. Due to this tip portion body fluid can be applied to the exposed portion of the test media tape very conveniently.

A sensing region is positioned between the supply portion and the storage portion to sense at least one property or analyte of the body fluid collected on the test media tape at the exposure portion of the cassette.

The testing device further may comprise a pricking unit for pricking a body portion. The lancing opening of that pricking unit advantageously can be arranged in or close to the convex portion so that the tip portion can be used for convenient pricking as well. The pricking unit may be arranged below the test media tape and a lancing device can either penetrate the test media tape or can extend through a recess in the test media tape.

A further aspect of the present invention is a method and a device for visual user guidance for application of body fluid samples. According to this embodiment the testing device comprises an illumination unit which indicates by illumination of a portion of a test element where body fluid is to be applied. The illumination serves for a timely and/or spatially guidance of the user to apply body fluid. Further the illumination may serve to indicate the location where to position a body portion for pricking. An illuminated area on the test medium may further indicate the amount (or the droplet size) of body fluid which is required by the testing device.

Another aspect of the present invention concerns a test cassette for collecting a body fluid sample. The cassette includes a test media tape, which has a section for receiving test media tape that is contaminated with past samples of the body fluid and a section for storing and providing uncontaminated test media tape. The cassette includes a housing that has a supply portion in which the uncontaminated section of the test media tape is enclosed. The housing further includes a storage portion in which the contaminated section of the test media tape is enclosed after contamination. The cassette further includes a convex tip portion over which the test media tape runs and at which the test media tape is exposed to the body fluid. A supply reel is disposed in the supply portion of the housing around which the uncontaminated section of the test media tape is wrapped. A storage reel is disposed in the storage portion of the housing around which the contaminated section of the test media tape is wrapped.

Further this invention concerns a method of using a testing device comprising the steps of
 a) bringing a test element into a sample application position,
 b) illuminating a portion of the test element onto which sample fluid application is desired, c) application of sample fluid to the illuminated portion,
d) evaluation of a test medium of the test element to generate an analytical result
e) withdrawing the test element or the test medium from the sample application position.

In case of an embodiment employing a test media tape a number of test media are located on the same test element (e.g. a tape). The steps for bringing a test element into a sample application position and removing it from this position in this case are made by shifting the position of the test element. It further has to be understood that step e) can be made prior to step d) if evaluation is performed at a different position than sample application.

In case of a device receiving single use test elements an individual test element is brought into the sample application position and is taken out of the device after use.

A further step may be included in the above method which concerns a pricking for generating a body opening.

Other forms, embodiments, objects, features, advantages, benefits and aspects of the present invention shall become apparent from the detailed drawings and description contained herein.

BRIEF DESCRIPTION OF THE DRAWINGS

FIG. 4: Cut trough a tip portion in plane with test media tape movement direction.

DESCRIPTION OF SELECTED EMBODIMENTS

Figure 1A:
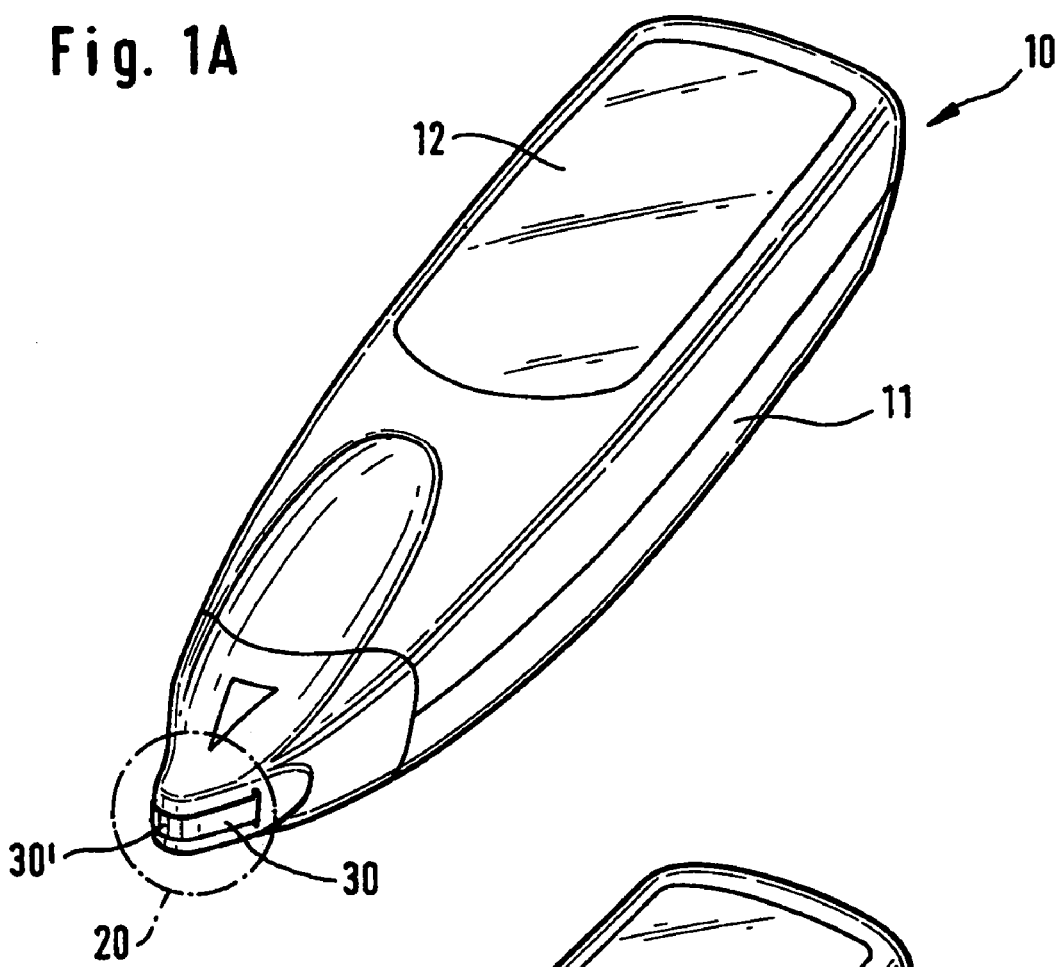
FIG. 1: Testing devices having a tip portion at their distal end.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the art that some of the features which are not relevant to the invention may not be shown for the sake of clarity.

A first general concept of the present invention concerns a body fluid testing device that incorporates a test media tape. The test media tape holds test media that are used to collect body fluid samples which are analyzed with a sensor. Advantageously the test media tape is housed in a cassette so that after the test media of a cassette are used up a fresh test media cassette can be inserted into the testing device. The test media tape is indexed before or after each test so that successive tests can be performed without requiring disposal of individual test media. The test media can be indexed manually or automatically.

The test medium is a medium which contains a test chemistry that with analyte from a sample leads to detectable results. For further details of test chemistry and testing see section "Testing General". Preferably the test media are designed to soak up the test fluid sample. This prevents the testing device from becoming contaminated by body fluid sample. As will be described in more detail later on it is preferred to employ a test media tape which comprises a transport tape on which test media are arranged with free spaces between successive test media. The preferred arrangement therefore has a structure with regions as follows: tape with test medium-tape without test medium—tape with test medium—and so on. The tape can be made e.g. from conventional plastic tape. The test media are attached to the tape, e.g. by gluing, welding or by use of an adhesive tape.

A body fluid testing device (10) according to the present invention is shown in FIG. 1A. The drawing of the device shows a housing (11) and a display (12) for displaying test results as well as instructions of use. At the front end of the device there can be seen a tip portion (20) over which the test media tape (30) runs. This tip portion is a first inventive idea of the present invention. A test medium at the front end of the testing device is exposed by the tip portion in a tip like manner which facilitates the application of body fluid. The tip portion for this reason at least partially projects out of the contour of the housing (11) of the testing device to be accessible for a body portion (e.g. finger or arm).

The testing device can be approached to a body surface (e.g. finger or arm) on which a body fluid sample is located with the tip portion. In order to make the tip portion easily accessible and visible as the location where sample has to be applied it is preferred to employ a tip like shape. Easy access and good visibility can be achieved by a tip portion that changes the direction of movement of the test media tape by an angle of more than 60 degree, preferably more than 90 degree.

Figure 1B:
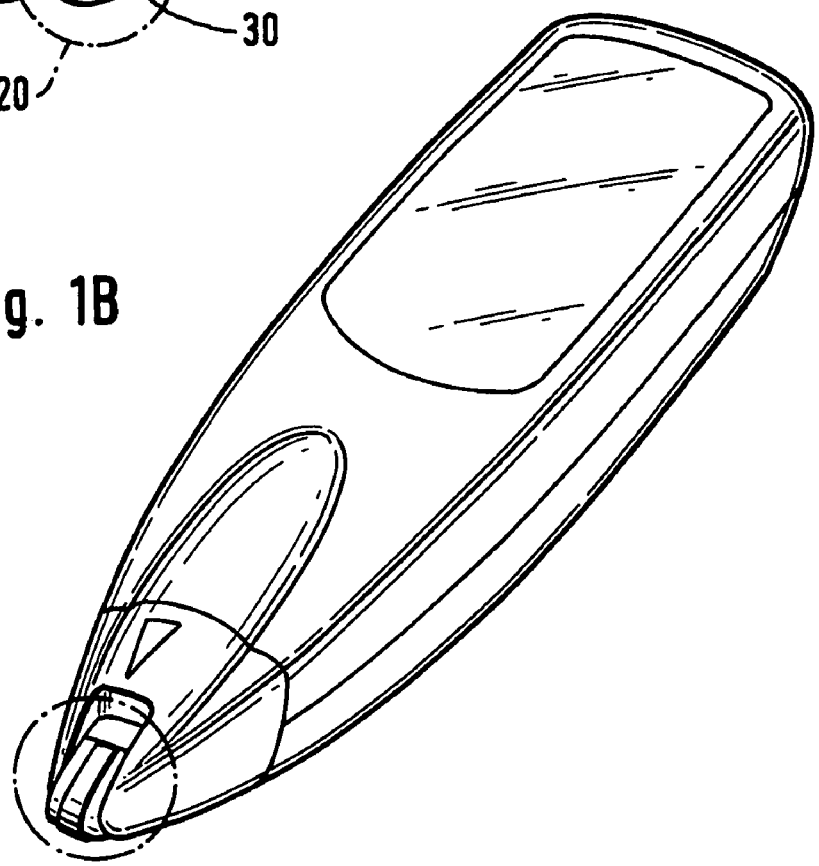

FIG. 1B shows a very similar testing device as depicted in FIG. 1A. While the test media tape (30) in the embodiment of FIG. 1A runs from the left to the right side of the device (or vice versa) in FIG. 1B the tape runs from the upper side to the lower side (or vice versa).

According to a second inventive concept of the present invention body fluid application can be further facilitated by illuminating a portion (30') of the test tape where the body fluid sample has to be applied. For this functionality a translucent test medium is advantageous. If the test medium, however, is opaque a translucent portion of the test media tape without test medium applied to it may be employed. However, most test media for analyte testing as e.g. reflectometric glucose test media are partially transparent and therefore produce an easily visible lighted area on the frontside of the test medium when illumination from the backside is made and the layer of test medium is not too thick. The artisan in this field knows how to make test media which transmit enough light that an illumination from the backside can easily be seen by a user. It is preferred to illuminate the backside of the test media tape with colored light (e.g. red or green) so that a better visible illumination results as by illumination with white light would result.

The second inventive concept of the present invention includes the user guidance by illuminating a portion of the test medium or a test element to which sample fluid has to be applied. As already described above illumination is made when the device is ready to receive sample fluid. Further the size of the illuminated area on the frontside of the test medium advantageously can be chosen to indicate the size of the test medium which needs to be filled with sample fluid to allow proper analysis. The user therefore can visually control whether he has applied enough sample fluid to the correct position on the test medium. The illumination for user guidance is made when the test element is positioned in the testing device for sample reception. For illumination the same optics as for optical evaluation can be used. However, if it is desired to indicate the size of sample fluid to be applied to the test medium it is preferred to employ a separate light source for this purpose or to employ means that change the size of illuminated area. For indication of application site and indication of desired sample volume in the latter case a first surface of the test medium is illuminated and a differently sized area (located within the first area) is illuminated for evaluating the test medium.

There is a certain connection between the area wetted by sample fluid and the recognition whether proper analysis can be done. Test media require a certain amount of sample volume to allow a reliable measurement. The amount of liquid which is necessary depends on a number of factors as the test chemistry, test architecture (layer structure with e.g. additional layers for removal of cells etc.), optics or electrodes and so on. For an actual testing device where these factors are fixed and the test medium is standardized the minimum amount of sample fluid needed for reliable measurement is a fixed number. On the other side the area on the test medium covered by sample fluid is related to the volume of sample fluid. In case of a non-absorbing test medium a drop is formed with an area that is dependent on surface tension. Based upon known surface conditions the area therefore can be related to the sample volume. In case of an absorbing test medium the absorption capacity per area determines the area which is wetted by a certain amount of fluid. The wetted area on the test medium therefore is closely related to the volume of fluid applied.

The testing device according to this second inventive idea illuminates an area of the test medium which becomes wetted when a sample volume equal or above the volume required for proper analysis is applied. The user therefore can visually control whether the fluid sample he has applied covers the whole illuminated area or not. This allows a twofold control
   if enough fluid has been applied
   if the body fluid sample has been applied to the correct location on the test medium.

Further it is advantageous to combine the user guidance by illumination with monitoring of fluid application to the test medium. Such monitoring is possible by optical or electrochemical detection. In an optical method light reflected from the test medium is detected and a change in intensity is monitored to detect sample fluid application. In an electrical process conductivity or capacity can be monitored to detect sample application. The before mentioned changes of measurement signals can be evaluated to give one or more of the following information:
   whether sample has been applied to the test medium,
   whether the sample has been applied to the correct position on the test medium
   whether the applied sample volume is sufficient.

Illumination at the tip portion further may serve to guide the user through the use process of the testing device. Blinking e.g. may indicate that the testing device is ready for sample fluid to be applied and a constant light or a deenergization of the light may show that sample has been successfully applied.

Illumination as described above can be implemented by employing a separate light source which is controlled by a control unit. However, in case of optical measurement as common in this field the light source for measurement can advantageously be employed for illumination of the test medium at the sampling position as well.

A testing device according to the above embodiment further has a control unit for controlling activation of the light source for illumination of the test medium. The control unit activates the light source when the instrument waits for fluid sample to be applied to the test medium. Illumination in this sense does not only mean constant illumination but also includes e.g. blinking. The illumination may remain until the user shuts down the testing device but it is preferred that the control unit deactivates illumination or changes the type of illumination when proper application of fluid to the test medium is detected (as described above). However, in case of optical evaluation of the test medium the illumination may be activated again for measuring an analyte concentration in the fluid sample.

The user guidance by illumination can be employed advantageously in embodiments where the test media portion for application of sample fluid is located at a tip. In this geometric setup the user can see the light when he is applying sample to the test medium. By sake of the tip geometry the user can visually monitor the application process, especially the approaching of the tip portion by a body portion on which body fluid is located. Due to illumination at the tip portion light is not shielded by the approaching body portion until shortly before contacting the illuminated area with sample fluid.

Figure 8:
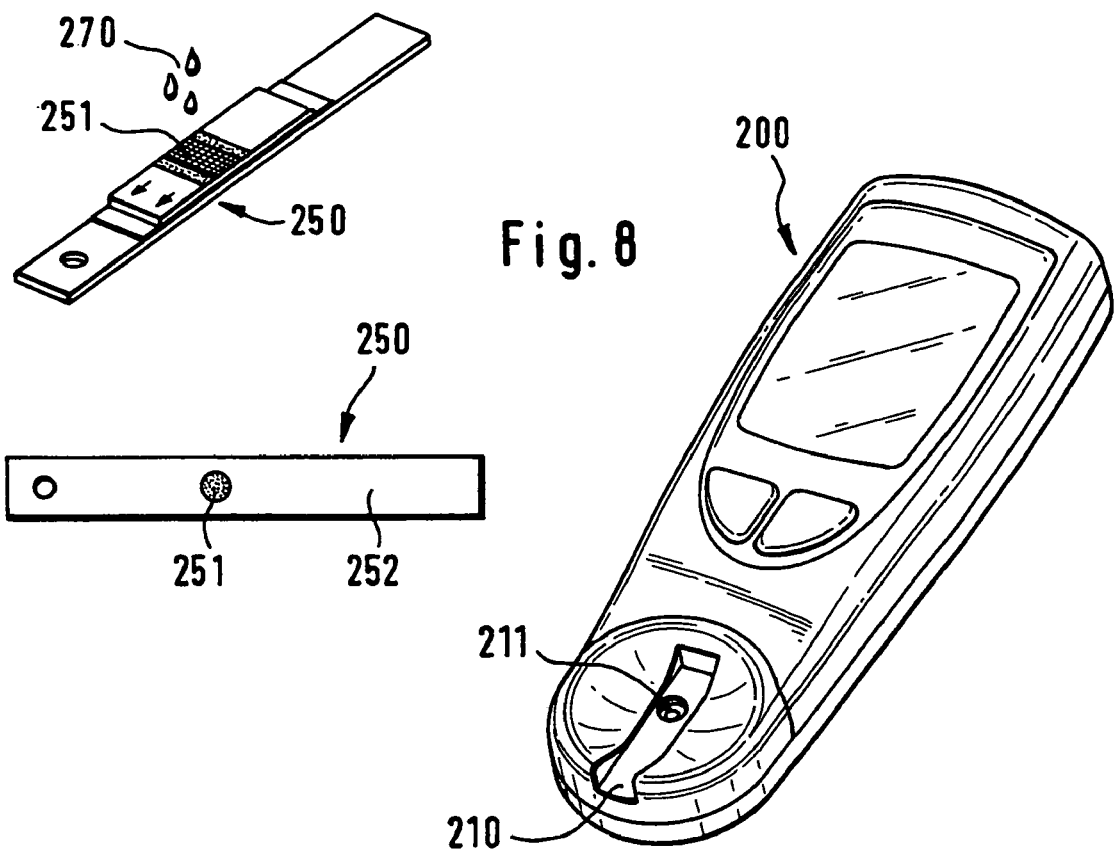
FIG. 8: Embodiments employing illuminated sample application zones.
Figure 9:
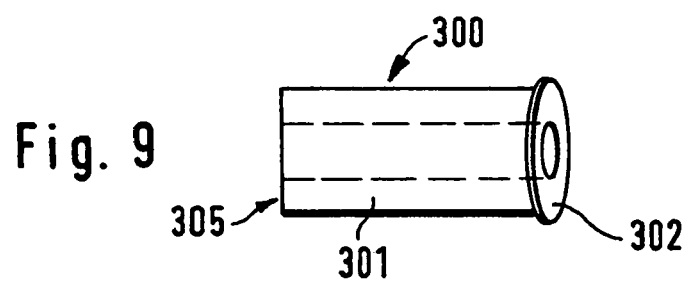
FIG. 9: Illumination concept applied to light guiding test element.
Figure 10:
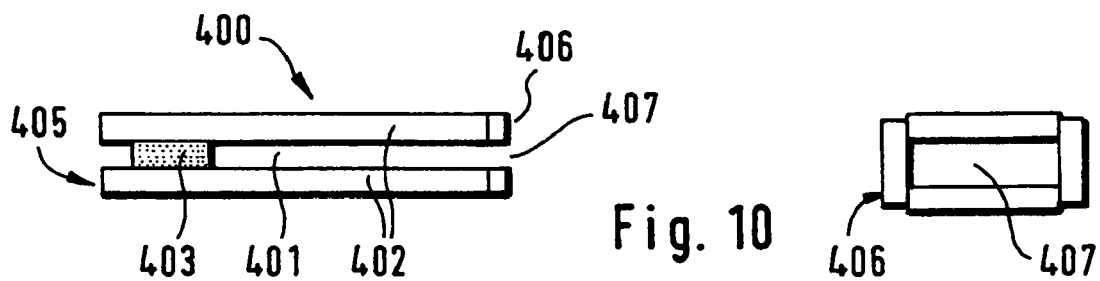
FIG. 10: Illumination concept applied to capillary fill test element.

However, the user guidance by illumination of the sample application area can be used in a much wider field as shown in FIGS. 8 to 10.

FIG. 8 depicts a reflectometric blood glucose testing device (200) which is sold under the name AccuChek Active™. The device has a port (210) for receiving individual test elements (250). A suitable test element is shown from the upper side and the backside. When the test element is arranged for measurement a test element (250) is located in the port (210) so that the backside of the test medium (251) is positioned above an optical sensing unit (211). The test medium changes color in dependence on analyte concentration in a sample fluid (270) which is applied to the upper side of the test medium. The backside of the test medium can be optically accessed through a recess in the test element base (252) to allow optical reading. In prior art systems illumination of the test medium is made for reading only but not for user guidance. Therefore the present invention claims the concept of user guidance for sample application by illuminating an area on the test medium. Advantageously in this context the indication of sample fluid size and guidance for positioning of the sample fluid by use of the illumination site as well as the illuminated area size as described above can be employed. Further it is preferred in this embodiment to employ a continuous illumination of the sample application zone which remains until sample is applied.

In FIG. 9 there is shown the illumination for user guidance concept in the context of a light guiding test element (300). The test element has the shape of a tube (301) made of light guiding material (e.g. a clear plastic as polymethylmethacrylate). On the front side of the tube there is located a test medium (301) onto which sample fluid needs to be applied for analysis. The backside of the tube is connected to an optics (not shown) for guiding light (305) into the tube and for receiving light reflected from the backside of the test medium (302). For user guidance illumination can be made in the same way by guiding light into the light guiding test element so that the test medium onto which fluid has to be applied is illuminated. It has to be understood that this invention is not restricted to tube shaped test elements but that it also can be applied to other light guiding test elements as well. Contrary to the conventional use of such light guiding test elements illumination is activated when the testing device is ready for sample reception and the illumination indicates to the user that sample has to be applied.

FIG. 10 shows the illumination for user guidance in a further context. The test element (400) is a capillary fill test element having a capillary channel (401) formed in a layer (402) of material. This layer (401) or a layer of material located above or below have light guiding properties. When light (405) is directed into the back end of the test element the frontside (406) of the test element is illuminated. Sample fluid is applied to the capillary end (407) at the frontside and the sample fluid moves through the capillary channel to the test medium (403). The test medium e.g. can be evaluated electrochemically by electrodes contacting the test medium. Alternatively the test medium can be read optically trough a recess in the test element. In this embodiment the sample is not directly applied to the test medium itself but to a transport capillary. The illumination indicates a portion of the test element to which sample has to be applied. However, the sample has to be applied to the capillary which is indicated by the illuminated end of the test element located next to the capillary end.

Figure 2:
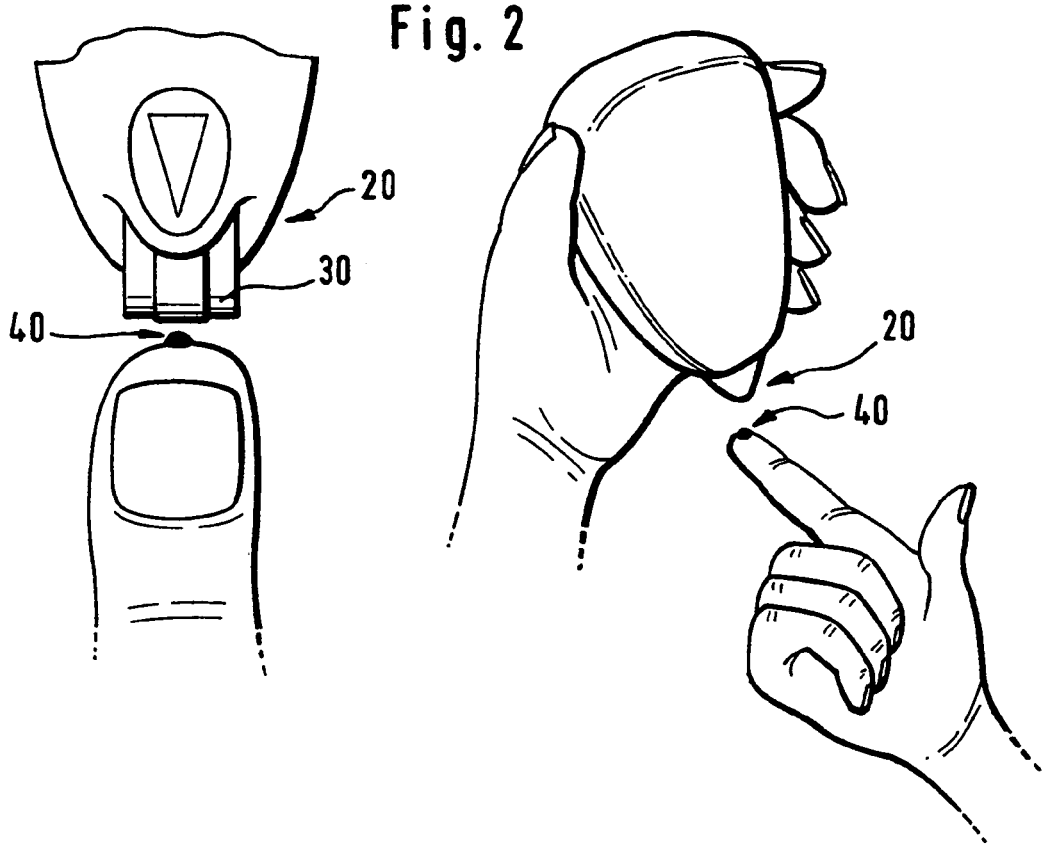
FIG. 2: Blood application to a tip portion with a finger tip.

FIG. 2 shows the application of body fluid (40) to an exposed portion of test media tape (30) at the convex tip portion (20) of a testing device. From the figures it can be seen how the tip portion facilitates sample application.

Figure 3:
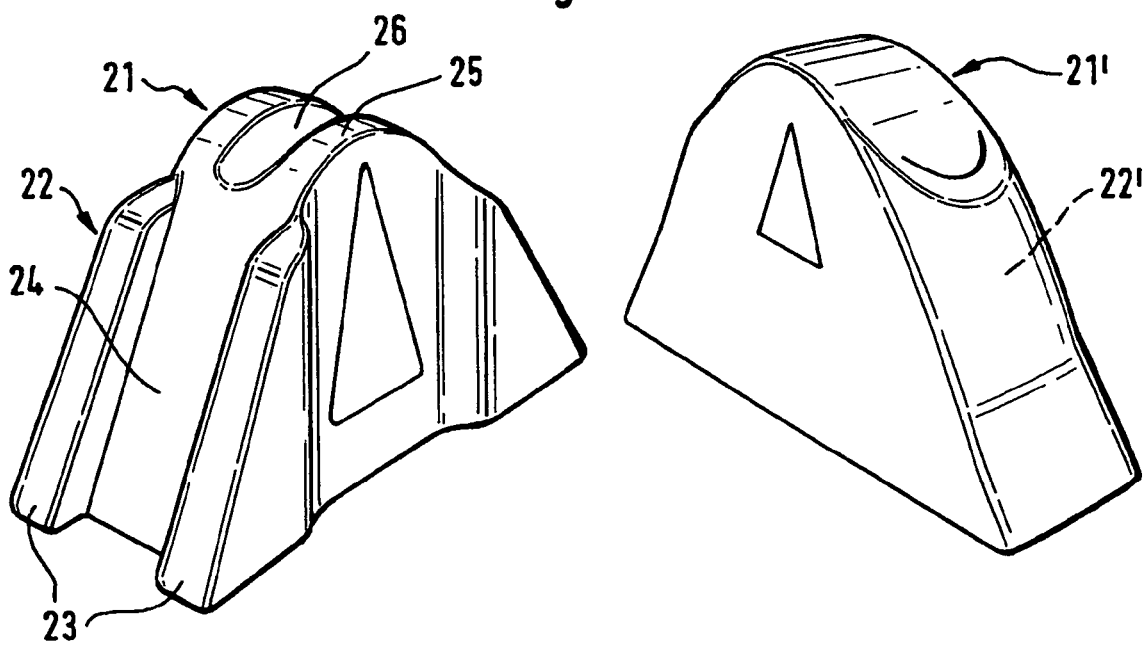
FIG. 3: Tip portion embodiments in perspective view.

FIG. 3 depicts two tip portion (20) embodiments in more detail. The embodiment of FIG. 3A has an exposure portion (21) and a guidance portion (22). The guidance portion (22) has a channel formed by two rails (23) which guide a test media tape for traveling on the bottom surface (24) of the channel. The exposure portion (21) preferably has no protruding elements as e.g. rails which could hinder contacting of the test media tape sited in this area with body fluid. The tape supporting surface (25) further has a recess (26) as depicted in FIG. 3A. In this recess a sensor can be disposed for evaluation of the test media tape. Suitable sensors are optical sensors including a light source and a detector for measuring light reflected from the test medium. Further a sensor unit with electrodes can be disposed in that recess (26) for contacting electrochemical test media at the exposure portion (21).

It is preferred to locate the sensing portion of a sensor unit at the exposure portion since measurement can be done right after the sample has been applied and no tape transport is necessary before measurement. However, it is also possible to locate a measurement unit for analyte concentration measurement at another position to which the test medium is moved after sample has been applied to it.

In FIG. 3B a tip portion (20) similar to that of FIG. 3A is shown. However, the guidance portion (22) has a circumferentially closed channel through which the test media tape runs. The tape is therefore guided by the inner walls of that channel to run over the exposure portion (21'). The exposure portion (21') is different to that of FIG. 3A in that it has no recess but a sensing unit is integrated into it. This can be accomplished by e.g. making a part or the whole exposure portion (21') from clear plastic to allow light to shine through it and to transmit light reflected from the test medium located over exposure portion (21') to a detector.

The tip portions (20) of FIGS. 3A and 3B can be a part of the testing device (10) or they can be a part of a test media tape cassette.

FIG. 4 shows a cut through tip portion (20) of FIG. 3B. In this perspective the guidance portion (22') in form of two channels left and right from the exposure portion (21') can be seen. The tip portion is made from an opaque plastic with an illumination channel (27) and a detection channel (28). At the proximal end of the illumination channel (27) a light source (50) (e.g. a LED) is disposed to illuminate a test medium located above the distal end of the illumination channel. Light reflected from the test medium enters the detection channel (28) at its distal end and is received by a detector (60) (e.g. a photovoltaic element or a photodiode) at the proximal end of the detection channel. Illumination channel and/or detection channel can be empty channels or channels in which optical elements as e.g. lenses or light transmitting fibers are located.

FIG. 4 further shows an important effect of the tip portion. The test media tape lies on the exposure portion (21') and enters this portion in the direction shown by a first arrow (ED) and leaves the portion in direction of a second arrow (LD). Right hand to the tip there is shown a vector diagram in which the starting point of these two direction vectors are located on the same spot. It can be seen that there is an angle between leaving direction (LD) and entering direction (ED). It has been found particularly suited to provide handling ease by employing an angle $\alpha$ above 60°, preferably above 90°. It has to be understood that this definition is not restricted to embodiments where the test media tape rests on the exposure portion. This definition is based on the change of direction which is imposed on the test media tape imposed by the tip portion, preferably within the exposure portion.

FIGS. 5A, B, C and D show possible arrangements of supply and storage portions for test media tape relative to the tip portion (20). In FIG. 5A a test media storage reel (110) is located behind the tip portion (20) and behind the storage reel a supply reel (100) is located. The positions of the supply and the storage reel can be exchanged vice versa while still having this in-line arrangement. The in-line arrangement is advantageous if a slim testing device is desired.

FIG. 5B depicts an embodiment where a supply (100) and a storage reel (110) are arranged side by side with the tip portion (20) in between. This arrangement is advantageous if the tip portion (20) is part of the instrument so that the test media tape (30) can be spanned over the tip portion during or after insertion of a test media cassette into the testing device.

FIG. 5C depicts a further alternative with two reels in a supply portion and two reels in the storage portion (110). The arrows in all these schematic diagrams indicate the direction of movement of the test media tape during subsequent use of portions of test medium. The embodiment of FIG. 5C is advantageous if a slim design of the testing device is desired. A view to FIG. 1 shows that a slim design facilitates user handling.

Figure 5D:
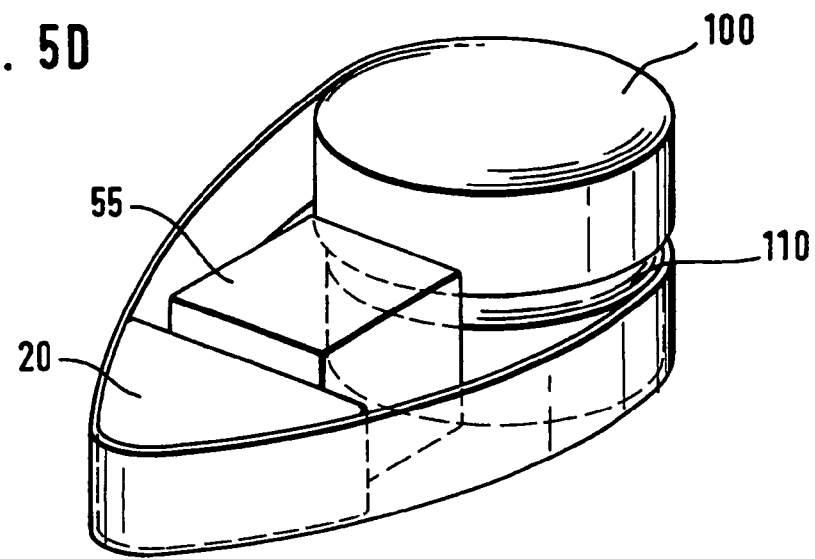
FIG. 5: Embodiments of supply and storage reel arrangements.
Figure 5D:
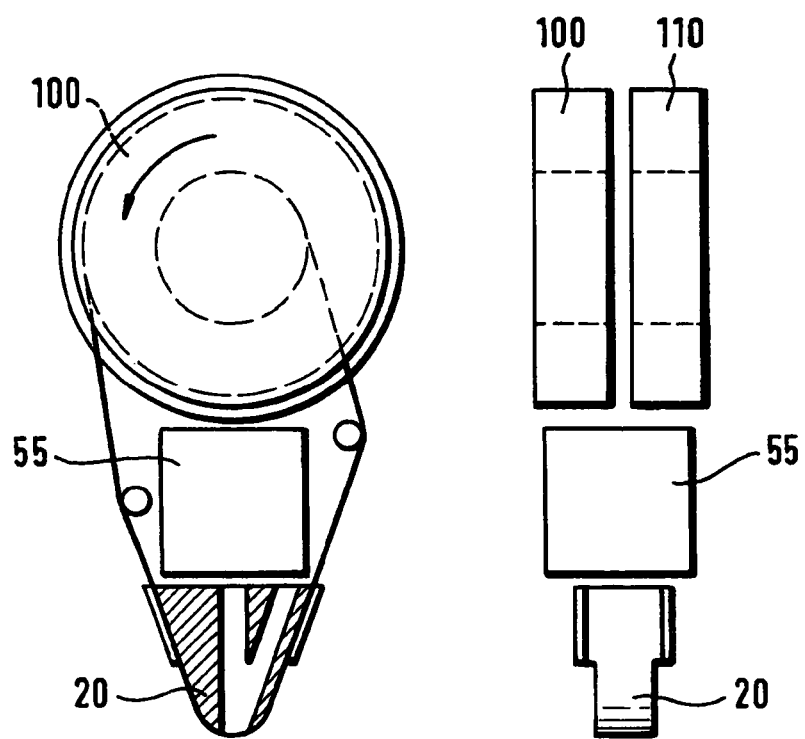
Figure 5D:
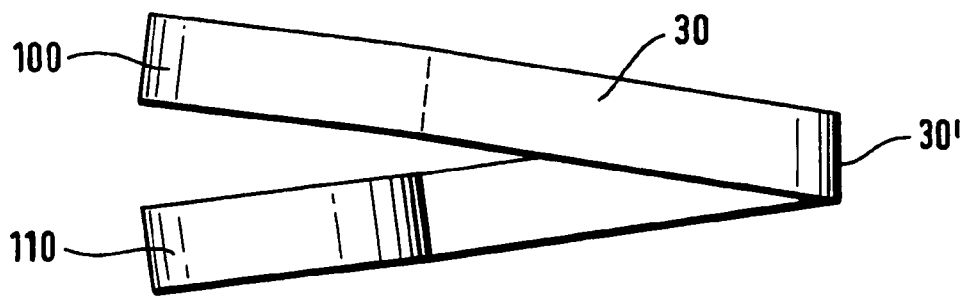

In FIG. 5D there is shown an embodiment where the supply and storage reel are arranged coaxially. As can be seen this arrangement is very space efficient. Between the reels and the tip portion (20) there is located an optical unit (55) for evaluating a test medium (30') located at the tip portion.

Figure 6A:
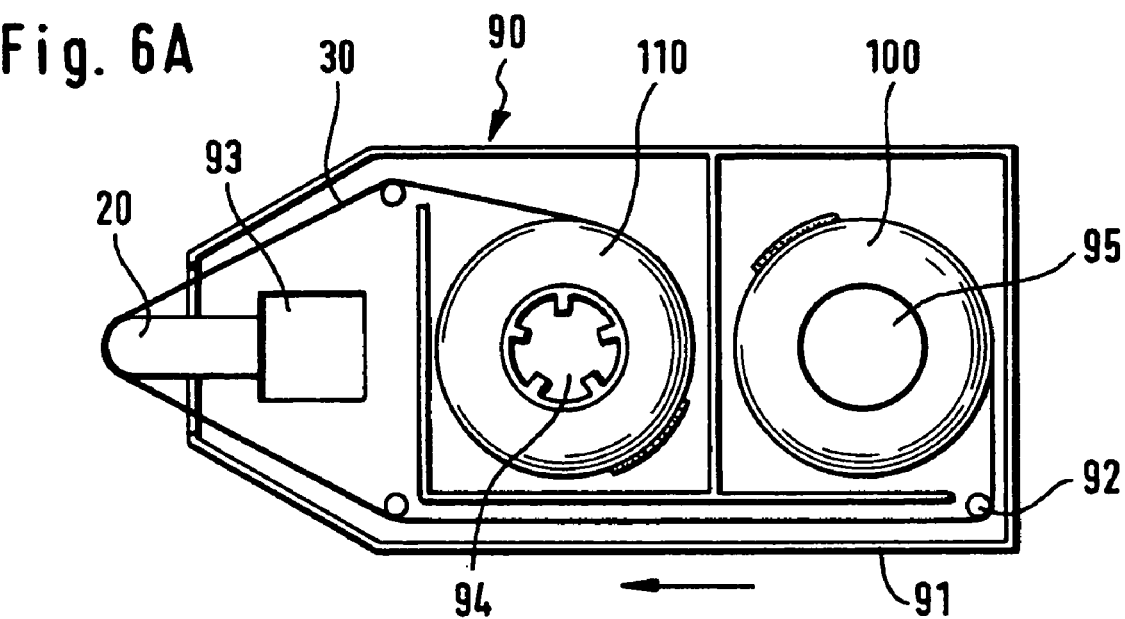
FIG. 6: Test media tape cassette with tip portion and testing device with inserted cassette.

In FIG. 6A there can be seen a test media cassette (90) for insertion into a testing device. The cassette has a housing (91) in which a supply reel (100) and a storage reel (10) are located. The cassette further comprises a tip portion (20). The test media tape (30) runs over the distal end (outer end) of the tip portion. The test media tape portion on the tip portion is located outside the housing (91) and therefore exposed to the surrounding. At the inner end (distal end) of the tip portion the cassette has a first recess (93) in its housing for receiving an optics belonging to the testing device. It is advantageous that the cassette has rollers or pins (92) for guiding the test media tape through the cassette. In the depicted embodiment the cassette has a second recess (94) for receiving a drive wheel of the testing device. The storage reel (110) has a recess in its center and engagement elements for receiving and engaging said drive wheel. It has to be understood that the drive wheel recess is an option only. Alternative an axis of the storage wheel can be employed which belongs to the cassette and which can be driven from outside the cassette.

The rotational axis (95) of the storage reel belongs to the cassette of the depicted embodiment. However, this axis can also be realized by a recess for receiving an axis belonging to the testing device. The supply reel (100) (or a drive which drives that reel) should have a tension control that controls tension of the test media tape and therefore avoids a too loose or too much tensioned test media tape.

As already mentioned the test media tape is exposed to the environment at the tip portion. Most test media are, however, destroyed or altered by humidity, sunlight etc. Therefore measures have to be taken to shelter the test media. A first measure is to package the whole cassette (90) before use such that a contact with humidity from the surrounding is prevented. This can be achieved by e.g. a blister package. Bearing in mind that the cassette housing (91) can be made as a body closed against humidity with the exception of the tip region embodiments can be contemplated which employ a humidity proof cover over the tip region which can be removed prior to use of the cassette.

Figure 6B:
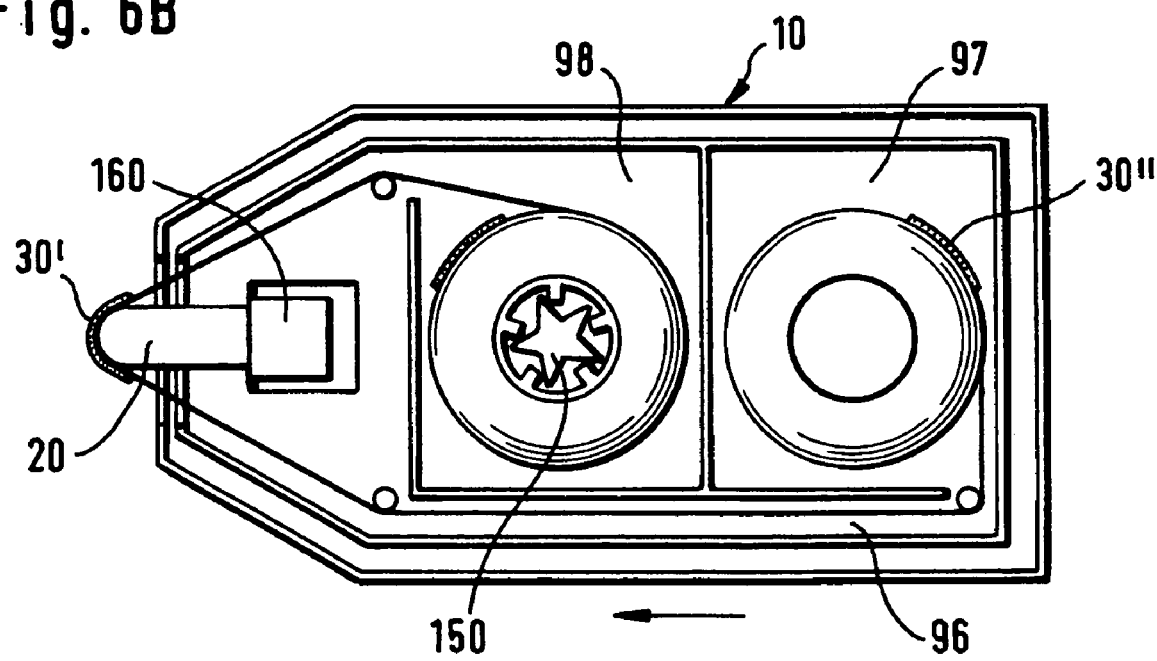

FIG. 6B shows a testing device (10) with the cassette (90) of FIG. 6A being inserted into it. The testing device has a drive wheel (150) engaging the storage reel (110) of the cassette. The drive wheel is driven by a motor (not shown). Alternative the drive wheel can be actuated manually by a user. When a motor is employed this can be actuated by a drive unit which controls and coordinates the transfer of test media into the sampling position on the tip portion (20) and measurement. As already mentioned it is advantageous to conduct an evaluation of a test medium wetted with sample fluid when the test medium is located at the tip portion. However, it is also possible to transfer a test medium wetted with sample fluid away from that position into a spatially distinct evaluation position, e.g. within the cassette. In FIG. 6B there can be further seen an optics (160) which belongs to the testing device and which enters the first recess (93) when the cassette (90) is inserted into the testing device (10). In case of optical measurement it is necessary to couple the device optics (160) with the tip portion (20). This e.g. can be accomplished by employing a tip portion as an optical transparent tip or to include optical fibers into an otherwise opaque tip (see e.g. FIG. 4). The device optics (160) can be made by use of fiber optics to which a light source and a detector are coupled.

FIG. 6B further shows an important measure to shelter test media against humidity and other influences when the cassette is already in use. As can be seen the distance of test media on the tape is chosen in a way that a second test medium (30") is located inside the cassette housing when a first test medium (30') is located on the tip portion (20). Further it is preferred if the distance between successive test media is so large that a successive test element is still within the sheltering housing when the actual test element is already located within the storage portion of the device. Even more advantageous the distance between two successive test media is so large that the second test medium is covered by overlying tape while the first test medium is on the tip portion. Hence the tape overlying the second test medium is sheltering it.

FIG. 6B further shows a channel (96) inside the cassette located between tip portion and supply portion. This channel is the only connection between the storage section (97) and the outside. Through this channel the test media tape runs from the storage reel on its way to the tip portion. Channel (96) serves to limit convections into the channel which would introduce humid air into the storage section in which fresh (unused) test media are stored. Further this channel serves as a diffusion channel which puts a resistance on the diffusion of humidity into the storage section.

FIG. 7 shows an alternative to the embodiment of FIG. 6. Here the differences between these two concepts will be described and for similarities reference is made to the description of FIG. 6.

Figure 7A:
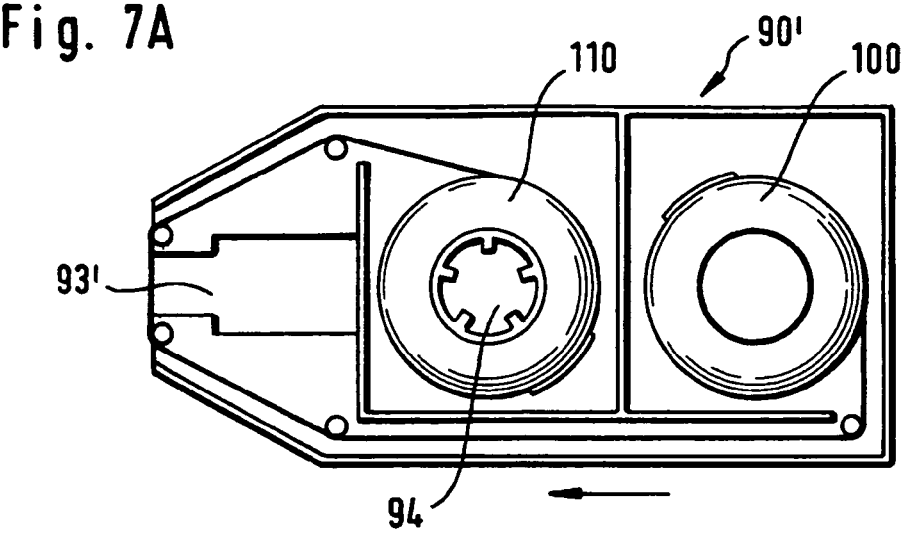
FIG. 7: Test media tape cassette and testing device having a tip portion with inserted cassette.

FIG. 7A depicts a test media cassette (90') having a supply reel (100) and a storage reel (110). The cassette has a first recess (93') for receiving an optics. This embodiment also has a second recess (94') for receiving a drive wheel similar to that described above. However, contrary to FIG. 6 the cassette of FIG. 7 has no tip portion.

Figure 7B:
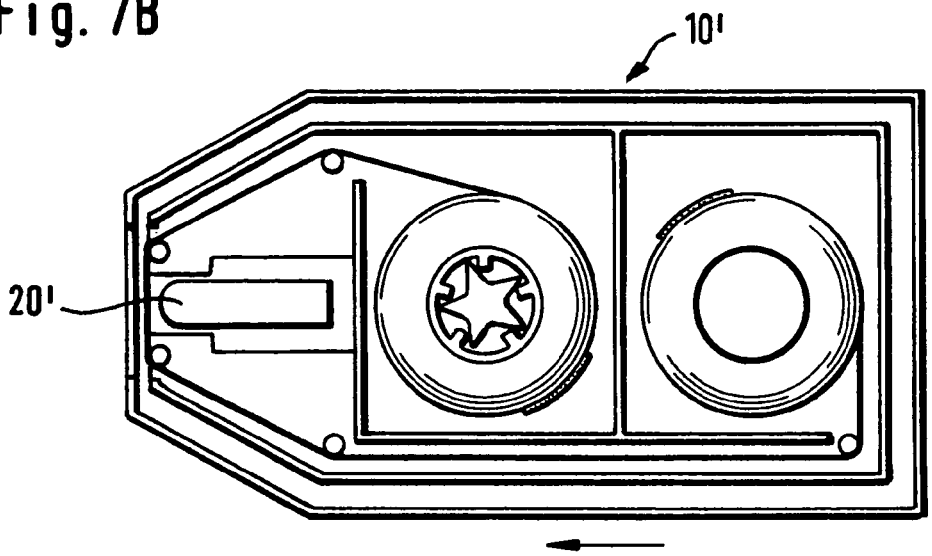
Figure 7C:
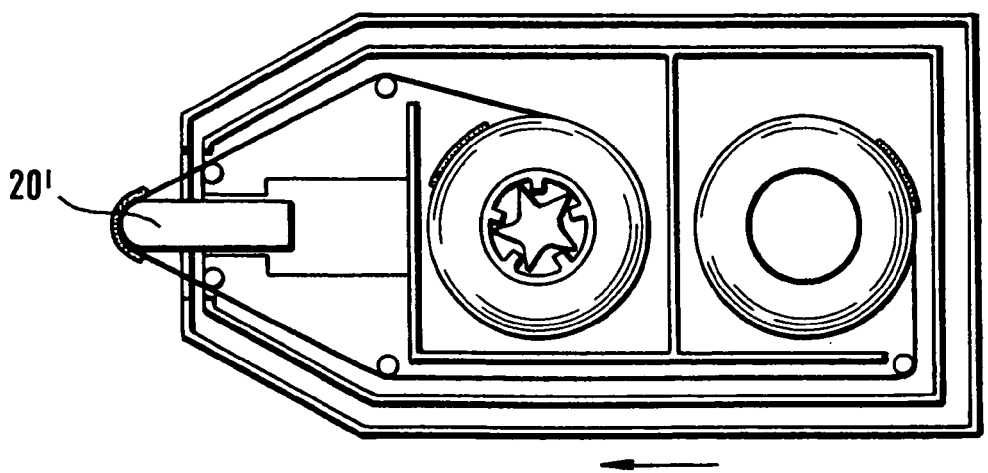

FIG. 7B shows the cassette of FIG. 7A inserted into a testing device (10'). As can be seen the testing device has a tip portion which is coupled to an evaluation optics of the testing device. As apparent from FIGS. 7A and 7B the cassette can be inserted into the testing device without user handling steps for guiding the test media tape onto the tip portion. With insertion the exposed portion of test media tape is already located in front of the tip portion (20') belonging to the testing device. From FIG. 7C it can be seen that the tip portion (20') is moved so that test media tape from the exposed portion is moved outside the device housing. Test media therefore can be accessed very easily by a user at the tip of the tip portion which extends outside the contour of the testing device.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are incorporated by reference as if each individual publication, patent, or patent application were specifically and individually indicated to be incorporated by reference and set forth in its entirety herein.

The invention claimed is:

1. A body fluid testing device for analyzing a body fluid, comprising:
    a test media tape adapted to collect the body fluid,
    a supply portion storing an uncontaminated section of the test media tape,
    a storage portion for storing a contaminated section of the test media tape,
    an exposure portion positioned between the supply portion and the storage portion, the exposure portion being adapted to expose a section of the test media tape to body fluid on a body surface,
    wherein said exposure portion has a tip portion for exposing a test medium of said test media tape to body fluid application and said tip portion imposing a change of direction to said tape which is above 60°, and the body fluid testing device further comprising optics coupled with the tip portion;
    said body fluid testing device having a housing with an outer contour;

wherein said tip portion at least partially extends outside the outer contour of said housing;

wherein said tip portion has an illumination channel and a detection channel;

a proximal end of said illumination channel has a light source to illuminate said test medium;

wherein said test medium is located above a distal end of said illumination channel; and wherein light reflected from said test medium enters said detection channel and is received by a detector.

2. The device of claim 1, wherein said tip portion is located at a distal end of the device.

3. The device of claim 1, wherein said test media tape is housed in a cassette.

4. The device of claim 1, wherein said tip portion comprises guiding means which guide the test media tape to avoid a slip of the tape off the tip portion.

5. The device of claim 4, wherein said guiding means are one or more guide rails or at least one channel.

6. The device of claim 1, wherein said tip portion includes at least one optical channel for illuminating a test medium and/or detecting light reflected by a test medium.

7. The device of claim 1, wherein:
the supply portion includes a supply reel, wherein the uncontaminated section of the test media tape is wound on the supply reel; and
the storage portion includes a storage reel, wherein the contaminated section of the test media tape can be wound on the storage reel.

8. The device of claim 1, further comprising a piercing device adapted to pierce skin.

9. The device of claim 8, wherein said piercing device is arranged to pierce a body portion located at the tip portion.

10. The device of claim 1 further comprising a sensor for sensing a change of a test medium induced by reaction with said body fluid.

11. The device of claim 10, wherein the sensor includes:
a light source and a detector;
a light transmission means coupled to the light source, the transmission means being adapted to transmit light from the light source onto a test medium; and
a light detection means the detection means being adapted to receive reflected light from said test medium and transmits the reflected light to the detector for analysis.

12. The device of claim 1, wherein said tip portion is part of the device.

13. The device of claim 1, wherein said tip portion is adapted to impose a change of direction to said tape which is above 60 degrees while said tape is external to said housing.

14. A test cassette for housing test media for sampling body fluid, comprising:
a section for receiving test media tape that is contaminated with past samples of the body fluid and an uncontaminated section;
a housing including a supply portion in which the uncontaminated section of the test media tape is enclosed, the housing further including a storage portion in which a contaminated section of the test media tape can be enclosed, the housing defining an exposure opening at which the test media tape is exposed to the body fluid;
wherein the test cassette further comprises a tip portion which guides the test media tape to expose a portion for body fluid application;
wherein said tip portion extends at least partially outside said housing to guide the test media tape to a position external to said housing;

wherein said tip portion has an illumination channel and a detection channel;

a proximal end of said illumination channel has a light source to illuminate said test medium;

wherein said test medium is located above a distal end of said illumination channel; and wherein light reflected from said test medium enters said detection channel and is received by a detector.

15. The test cassette of claim 14, wherein said housing has a recess for receiving a sensor belonging to a testing device.

16. The test cassette of claim 14, wherein said cassette has a channel which forms the sole air connection between the storage portion and the surroundings of the cassette.

17. The cassette of claim 16, wherein successive test media on the test media tape have a distance, said distance being chosen that when a first test medium is located on the tip portion the successive test element is located within the storage portion being sheltered from humidity by said channel.

18. The cassette of claim 14, wherein successive test media on the test media tape have a distance, said distance being chosen that when a first test medium is located on the tip portion the successive test element is located within the housing of the test cassette.

19. The cassette of claim 18, wherein said distance is chosen so that when a first test element is located on the tip portion the successive test element is covered by overlying tape.

20. A body fluid testing device for analyzing a body fluid, comprising:
a test media tape adapted to collect the body fluid,
a supply portion for storing an uncontaminated section of the test media tape,
a storage portion for storing a contaminated section of the test media tape,
an exposure portion positioned between the supply portion and the storage portion, the exposure portion being adapted to expose a section of the test media tape to the body fluid;
said testing device further comprising a light source for illuminating an area of the test media tape located within said exposure portion to guide a user for body fluid application;
said body fluid testing device further comprising a housing with an outer contour and a tip portion over which said test media tape runs at said exposure portion;
wherein said tip portion at least partially extends outside said outer contour of said housing;
wherein said tip portion has an illumination channel and a detection channel;
a proximal end of said illumination channel has a light source to illuminate said test medium;
wherein said test medium is located above a distal end of said illumination channel; and
wherein light reflected from said test medium enters said detection channel and is received by a detector.

21. The testing device of claim 20, wherein said light source is a light source for illuminating the test media tape for analysis of body fluid.

22. The testing device of claim 20, wherein said illuminated area is the area to which body fluid has to be applied.

23. The testing device of claim 20, further having a control unit controlling activation of said light source, said control unit activating said light source when the testing device desires a body fluid sample to be applied to the test media tape.

24. The testing device of claim 20, wherein said light source illuminates an area which corresponds to a volume of body fluid required for proper analysis.

25. A system for analyzing a body fluid, comprising:
- a body fluid testing device having a housing with an outer contour;
- a test media tape adapted to collect the body fluid;
- a supply portion storing an uncontaminated section of the test media tape inside the housing;
- a storage portion for storing a contaminated section of the test media tape inside the housing;
- a convex tip portion over which the test media tape runs between the supply portion and the storage portion;
- the convex tip portion at least partially projecting outside the outer contour of the housing to expose a section of the test media tape to the body fluid outside the housing of the body fluid testing device;
- wherein said convex tip portion has an illumination channel and a detection channel;
- a proximal end of said illumination channel has a light source to illuminate said test medium;
- wherein said test medium is located above a distal end of said illumination channel; and
- wherein light reflected from said test medium enters said detection channel and is received by a detector.

26. The system of claim 25, further comprising a sensor to analyze the fluid collected on the test media tape.

27. The system of claim 25, wherein the test media tape has successive test media spaced apart a distance where a first test medium is located on the convex tip portion and a second test medium is located within the housing.

28. The system of claim 25, further comprising:
- the convex tip portion including an illumination channel and a detection channel;
- a light source aligned with the illumination channel to illuminate at least part of the section of the test media tape located outside of the housing; and
- a detector aligned with the detection channel to receive the light from the light source that is reflected from the test media tape.

29. The system of claim 28, wherein the light source is configured to illuminate an area of the test media tape that corresponds to an area to be wetted by the body fluid to allow proper analysis by the detector.

30. The system of claim 28, wherein the body fluid testing device comprises a control unit for controlling activation of the light source when the body fluid testing device requires the body fluid for analysis.

31. The system of claim 25, wherein the test media tape has light guiding properties and the body fluid testing device guides light into the test media tape so that a portion of the test media tape onto which the body fluid is applied is illuminated.

* * * * *